(12) United States Patent
Tucker et al.

(10) Patent No.: US 6,743,921 B2
(45) Date of Patent: Jun. 1, 2004

(54) PROCESS FOR THE PREPARATION OF NONRACEMIC SYN-1-(4-HYDROXY-PHENYL)-2-(4-HYDROXY-4-PHENYL-PIPERIDIN-1-YL)-1-PROPANOL COMPOUNDS

(75) Inventors: Charles E. Tucker, Superior, CO (US); Qiongzhong Jiang, Sunnyvale, CA (US)

(73) Assignees: DSM Catalytica Pharmaceuticals, Inc., Greenville, NC (US); Pfizer, Inc., New York, NY (US)

( * ) Notice: Subject to any disclaimer, the term of this patent is extended or adjusted under 35 U.S.C. 154(b) by 0 days.

(21) Appl. No.: 10/057,826

(22) Filed: Jan. 24, 2002

(65) Prior Publication Data

US 2003/0144521 A1 Jul. 31, 2003

(51) Int. Cl.$^7$ .............................................. C07D 211/52
(52) U.S. Cl. ...................... 546/217; 514/315; 514/327; 514/456; 558/70
(58) Field of Search .......................... 546/217; 558/70; 514/315, 327, 456

(56) References Cited

U.S. PATENT DOCUMENTS

| | | | |
|---|---|---|---|
| 4,321,414 A | 3/1982 | Costa | |
| 5,716,961 A | 2/1998 | Sands | |
| 5,763,688 A | 6/1998 | Ikariya et al. | |
| 6,037,500 A | 3/2000 | Zhang | |
| 6,258,827 B1 * | 7/2001 | Chenard et al. | 514/327 |
| 6,372,931 B1 | 4/2002 | Blacker et al. | |
| 6,380,416 B2 * | 4/2002 | Zhang | 558/156 |
| 6,399,787 B1 | 6/2002 | Zhang | |
| 6,486,337 B2 | 11/2002 | Burk et al. | |
| 6,570,018 B2 * | 5/2003 | Walinsky et al. | 546/217 |
| 6,645,986 B2 * | 11/2003 | Walinsky et al. | 514/327 |
| 2002/0016465 A1 | 4/2001 | Walinsky et al. | |
| 2002/0016466 A1 | 4/2001 | Walinsky et al. | |
| 2001/0007872 A1 * | 7/2001 | Menniti et al. | 514/278 |
| 2002/0072538 A1 * | 7/2002 | Chenard et al. | 514/456 |
| 2002/0095058 A1 | 7/2002 | Cobley et al. | |

FOREIGN PATENT DOCUMENTS

| | | |
|---|---|---|
| EP | 0 901 977 A1 | 3/1999 |
| EP | 0 901 997 | 3/1999 |
| WO | WO 98/42643 | 10/1998 |
| WO | WO 00/18708 | 4/2000 |
| WO | WO 01/12574 | 2/2001 |
| WO | WO 01/23088 | 4/2001 |

OTHER PUBLICATIONS

U.S. patent application Ser. No. 10/153,421, Tucker et al., filed May 21, 2002.
U.S. patent application Ser. No. 10/158,559, Tucker et al., filed May 21, 2002.
U.S. patent application Ser. No. 10/158,560, Tucker et al., filed May 21, 2002.

Abdur–Rashid et al., "Catalytic cycle for the asymmetric hydrogenation of prochiral ketones to chiral alcohols: direct hydride and proton transfer form chiral catalysts trans–Ru(H)$_2$(diphosphine)(diamine) to ketones and direct addition of dihydrogen to the resulting hydridoamido complexes" J. Am. Chem. Soc. 123:7473–7474 (2001).
Cao, et al., "Ru–BICP–Catalyzed Asymmetric Hydrogentation of Aromatic Ketones" CA 130:281548 (1999).
Cross, David J. et al., "Rhodium Versus Ruthenium: Contrasting Behavior In The Asymmetric Transfer Hydrogenation Of A–Substituted Acetophenones", Tetrahedron: Asymmetry, 12:1801–1806 (2001).
Llorca et al., "Dichloro d–methionine–N,S–platinum II at 130K" Acta Crystallographica Section C 804–806 (2001).
Rossen, K., "Ru– and Rh–Catalyzed Asymmetric Hydrogenations: Recent Suprises from an Old Reaction", Angew: Chem., Int. Ed., 40:(24): 4611–4613 (2001).
Winter et al., "Trapping of butatrienylidene complexes with functional temary amines", CA 1997:487599 (1997).
Cao, P., et al., "Ru–BICP–Catalyzed Asymmetric Hydrogentation of Aromatic Ketones," J. Org. Chem., 64:2127–2129 (1999).
Doucet, H, et al., "trans–[RuCl$_2$(phosphane)$_2$(1,2–diamine)] and Chiral trans–RuCl$_2$(diphosphane)(1,2–dia–mine): Shelf–Stable Precatalysts for the Rapid, Productive, and Stereoselective Hydrogenation of Ketones," Angew. Chem. Int. Ed., 37(12):1703–1707. (1998).
Grey, et al., "Symposium on Homogeneous Catalysis Presented Before the Division of Petroleum Chemistry, Inc.," Am. Chem Soc., "Novel Anionic Phosphine Transition Metal Hydride Complexes and their Application to the Catalytic Hydrogenation of Polar Organic Compounds," 399–403 (1980).
Hartmann, R., et al., "Noyon's Hydrogenation Catalyst Needs a Lewis acid Cocatalyst for High Activity," Angew. Chem. Int. Ed., 40(19)3581–3585 (2001).
Hashiguchi, S., et al., Asymmetric Transfer Hydrogenation of Aromatic Ketones Catalyzed by Chiral Ruthemium (II) Complexes, J. Am. Soc., 117:7652–7563 (1995).
Jiang, Y., et al., "A New Chiral Bis(oxazolinylmethyl)amine Ligand for Ru–Catalyzed Asymmertic Transfer Hydrogenation of Ketones," J. Am. Chem. Soc., 120:3817–3818 (1998).
Lauhon T., et al., "RNA Aptamers that Bind Flavin and Nicotinamide Redox Confactors," J. Am. Chem. Soc., 117(4)1246–1257 (1995).

(List continued on next page.)

Primary Examiner—Celia Chang
(74) Attorney, Agent, or Firm—Townsend and Townsend and Crew LLP

(57) ABSTRACT

The present invention provides a process for the preparation of a nonracemic diastereomer of 1-(4-benzoxy-phenyl)-2-(4-hydroxy-4-phenyl-piperidin-1-yl)-1-propanol by hydrogenation of a corresponding nonracemic 1-(4-benzoxyphenyl)-2-(4-hydroxy-4-phenyl-piperidin-1-yl)-1-propanone using a catalyst system comprising ruthenium, a nonracemic diphosphine ligand, a bidentate amine ligand selected from amino-thioethers and achiral diamines, and a base.

20 Claims, No Drawings

OTHER PUBLICATIONS

Matsumura, K., et al., "Asymmetric Transfer Hydrogenation of α, β–Acetylenic Ketones," *J. Am. Chem. Soc.,* 119:8738–8739 (1997).

Mikami, K. et al., "Asymmetric Activation/Deactivation of Racemic Ru Catalysts for Highly Enantioselective Hydrogenation of Ketonic Substrates," *Angew. Chem. Int. Ed.,* 39(20):3707–3710 (2000).

Noyori, R., et al., "Asymmetric Catalysis by Architectural and Functional Molecular Engineering: Practical Chemo–and Stereoselective Hydrogenation of Ketones," *Angew Chem. Int.,* 40:40–73 (2001).

Noyori, R., Asymmetric Hydrogenation, *Acta Chem. Scandinavia,* 50:380–390 (1996).

Ohkuma, T., et al., "Asymmetric Activation of Racemic Ruthenium (II) Complexes for Enantloselective Hydrogenation," *J. Am. Chem. Soc.* 120:1088–1087 (1998).

Ohkuma, T., et al., Practical Enantioselective Hydrogenation of Aromatic Ketones, *J. Am. Chem. Soc.,* 117:2675–2676 (1995).

Ohkuma T., et al., "Asymmetric Hydrogenation of Alkenyl, Cyclopropryl, and Aryl Ketones, RuCl₂(xylbinap)(1,2–diamine) as a Precatalyst Exhibiting a Wide Scope," *J. Am. Chem. Soc.* 120:13529–13530 (1998).

Ohkuma, T., et al., "Asymmetric Hydrogenation of Cyclic α, β–Unsaturated Ketones to Chiral Alylic Alcohols," *SYN-LETT,* 467–468 (1997).

Ohkuma, T., et al., "General Asymmetric Hydrogenation of Hetero–aromatic Ketones," *Organic Letters,* 2(12)1749–1751 (2000).

Ohkuma, T., et al, "Practical Enantioselective Hydrogenation of Aromatic Ketones," *J. Am. Chem. Soc.* 117:2675–2676 (1995).

Ohkuma, T., et al., "Preferential Hydrogenation of Aldehydes and Ketones," *J. Am. Chem. Soc.,* 117:10417–10418 (1995).

Ohkuma, T., et al., "Stereoselective Hydrogenation of Simple Ketones Catalyzed by Ruthenium (II) Complexes," *J. Org. Chem.,* 61:4872–4873 (1996).

Püntener, K., et al., "New Efficient Catalysts for Enantioselective Transfer Hydrogenations," *Tetrahedron Letters,* 37(45):8165–8168 (1996).

R. A. Sánchez–Delgado, et al., "Chemistry and Catalytic Properties of Ruthenium and Osmium Complexes, 3. Development of Highly Active Systems for the Homogeneous Hydrogenation of Aldehydes and Ketones," *Inorg. Chem.,* 25:1106–1111 (1986).

R.A. Sánchez–Delgado, et al., "Homogeneous Hydrogenation of Ketones to Alcohols with Ruthenium complex Catalysts," 202:427–434 (1980).

R.A. Sánchez–Delgado, et al., "Homogeneous Hydrogenation of Aldehydes and Ketones by Use of Ruthenium Triphenylphosphine Complexes," *J. Mol. Catalysis,* 6:303–305 (1979).

Sammakia, T., et al., "Transfer Hydrogenation with Ruthenium Complexes of Chiral (Phosphinoferrocenyl) oxazolines," *J. Org. Chem.,* 62:6104–6105 (1997).

Takehara, J., et al., Amino alcohol on the ruthenium (II)–castalysed asymmetric transfer hydrogenation of ketones in propan–2–o1, *Chem. Commun.,* 233–234 (1996).

Yang, H., et al., "Ruthenium(II) Complexes with New Tridentate Ligands containing P, N, O Donor Atoms: Highly Efficient Catalysts for Transfer Hydrogenation of Ketones by Propan–2–o1.," *J. Chem. Soc., Commun.,* 172–1722 (1995).

\* cited by examiner

PROCESS FOR THE PREPARATION OF NONRACEMIC SYN-1-(4-HYDROXY-PHENYL)-2-(4-HYDROXY-4-PHENYL-PIPERIDIN-1-YL)-1-PROPANOL COMPOUNDS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

FIELD OF THE INVENTION

This invention relates generally to preparing nonracemic chiral alcohols. It is directed to a novel process for the preparation of a nonracemic diastereomer of 1-(4-hydroxy-phenyl)-2-(4-hydroxy-4-phenyl-piperidin-1-yl)-1-propanol compounds of the formula I or a stereoisomer thereof, wherein R is hydrogen or a hydroxyl-protecting group.

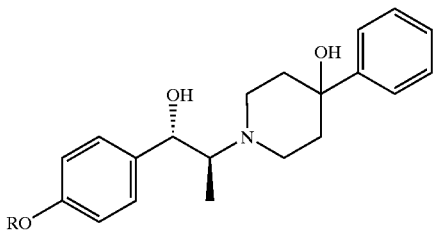

I

This invention more specifically relates to preparing non-racemic chiral alcohols by asymmetric hydrogenation of ketones. It is directed to the preparation of compounds of the formula I by asymmetric hydrogenation of the corresponding nonracemic ketone compound of formula II or its enantiomer.

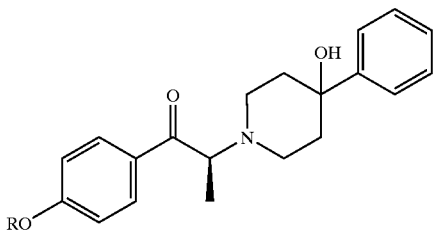

II

Compounds of formula I are useful as pharmaceutically active compounds and as intermediates thereto. For example, the nonracemic compound of formula I having the (1S,2S) stereochemical configuration, wherein R is hydrogen, exhibits potent NMDS (N-methyl-D-aspartic acid) receptor antagonist activity and is useful in the treatment of traumatic brain injury and other central nervous system conditions. Corresponding compounds wherein R is an alkyl group or a hydroxyl-protecting group are useful in the preparation of the compound of formula I wherein R is hydrogen.

BACKGROUND OF THE INVENTION

Ketones can be converted to racemic chiral alcohols by hydrogenation using certain catalyst systems of ruthenium, a phosphine ligand, a 1,2-diamine, and an alkaline base. Aromatic and heteroaromatic ketones can be hydrogenated to nonracemic chiral alcohols by using certain catalyst systems of ruthenium, an appropriate enantiomeric diphosphine ligand, an enantiomeric 1,2-diamine, and an alkaline base. *Angew. Chem. Int. Ed.*, vol. 40, (2001), 40–73; U.S. Pat. No. 5,763,688; *J. Am. Chem. Soc.*, vol. 117 (1995), 2675–2676; *J. Org. Chem.*, vol. 64 (1999), 2127–2129. Similarly, such ketones can be hydrogenated to nonracemic chiral alcohols by using corresponding catalyst systems formed using a racemic chiral 1,2-diamine, wherein the active diastereomeric ruthenium catalyst is formed with the enantiomeric diphosphine ligand and the "matched" enantiomer of the racemic chiral 1,2-diamine, and the diastereomeric ruthenium complex with the "unmatched" enantiomer of the racemic chiral 1,2-diamine, if it is formed, is relatively inactive. *Angew. Chem. Int. Ed.*, vol. 40, (2001), 40–73; European Patent Application 0,901,977; *J. Am. Chem. Soc.*, vol. 120 (1998), 1086–1087. A catalyst system of ruthenium, S-2,2'-bis(diphenyl-phosphino)-1,1'-binaphthyl (S-BINAP), achiral ethylene diamine, and potassium hydroxide in isopropanol is reported to hydrogenate 1'-acetonaphthone to (R)-1-(1-naphthyl)ethanol in 57% enantiomeric excess. The corresponding catalyst system having enantiomeric (S,S)-1,2-diphenyl-ethylenediamine instead of achiral ethylene diamine is reported to hydrogenate 1'-acetonaphthone under the same conditions to (R)-1-(1-naphthyl)ethanol in 97% enantiomeric excess. *Angew. Chem. Int. Ed.*, vol. 40, (2001), 40–73; *J. Am. Chem. Soc.*, vol. 117 (1995), 2675–2676.

An earlier method (U.S. Pat. No. 5,716,961) for the preparation of enantiomeric (1S,2S)-1-(4-hydroxy-phenyl)-2-(4-hydroxy-4-phenyl-piperidin-1-yl)-1-propanol (formula I, R=H) involves the steps of: 1) a hydride reduction of the racemic ketone corresponding to formula II having R=benzyl to produce the racemic syn-enantiomers (equal parts (1S,2S) and (1R,2R) configurations) of formula I having R=benzyl; 2) debenzylation by catalytic hydrogenolysis to produce the racemic syn-enantiomers of the formula I having R=H; 3) diastereomeric salt resolution of the racemic syn-enantiomers using D-(−)-tartaric acid to produce the D-tartrate salt of the (1S,2S)-enantiomer of formula I having R=H; and 4) neutralization of the D-tartrate salt to produce the free base (1S,2S)-1-(4-hydroxy-phenyl)-2-(4-hydroxy-4-phenyl-piperidin-1-yl)-1-propanol (formula I, R=H). The free base is further reacted with methanesulfonic acid to produce the mesylate salt trihydrate. In this method, half of the racemic mixture of syn-enantiomers formed in the first step has the undesired (1R,2R) stereoconfiguration, which must be separated and discarded in the subsequent resolution step.

A related application (U.S. Ser. No. 09/840,580 filed Apr. 23, 2001), describes process improvements which allow a more efficient D-(−)-tartaric acid resolution of the syn-enantiomers and allows the direct conversion of the D-(−)-tartrate salt to the mesylate salt without intermediate conversion to the free base.

In a related application (Ser. No. 09/840,668 filed on Apr. 23, 2001) both enantiomers of the racemic ketone starting material are converted into a diaroyl D-tartrate salt of the (2S)-enantiomer (formula II, R=benzyl) by a dynamic resolution using a diaroyl D-tartaric acid. After neutralization to the free base, the enantiomerically pure ketone is reduced with hydride to produce the (1S,2S)-enantiomer of formula I having R=benzyl. Debenzylation produces (1S,2S)-1-(4-hydroxy-phenyl)-2-(4-hydroxy-4-phenyl-piperidin-1-yl)-1-propanol (formula I, R=H), which is subsequently converted to its mesylate salt. The dynamic resolution of the ketone, in which both enantiomers are converted into one, avoids the wasteful resolution of the alcohol in the earlier process, in which the undesired enantiomer is discarded.

SUMMARY OF THE INVENTION

The present invention provides a process for the preparation of a nonracemic chiral alcohol by hydrogenation of a ketone using a catalyst system comprising ruthenium, a nonracemic chiral diphosphine ligand, a bidentate amine ligand selected from an amino-thioether and an achiral diamine, and a base. The inventors have surprisingly found, contrary to the teachings of the background references, that a chiral diamine ligand is not required to obtain highly enantioselective hydrogenation of a ketone to a nonracemic chiral alcohol when using a catalyst system comprising ruthenium, a nonracemic chiral diphosphine ligand, an amine ligand and a base. Accordingly, the present invention provides highly enantioselective hydrogenation of a ketone to a nonracemic chiral alcohol using a bidentate amine ligand selected from a monoamine-thioether and an achiral diamine, when using a catalyst system also comprising ruthenium, a nonracemic chiral diphosphine ligand, and a base.

In one group of embodiments the base is selected from alkylguanidines, aminophosphazenes, and proazaphosphatranes.

In one particular embodiment, the present invention provides a process for the preparation of a nonracemic diastereomer selected from 1-(4-hydroxy-phenyl)-2-(4-hydroxy-4-phenyl-piperidin-1-yl)-1-propanol having the structural formula I and stereoisomers thereof, wherein R is hydrogen or a hydroxyl-protecting group by hydrogenation of a corresponding nonracemic 1-(4-hydroxy-phenyl)-2-(4-hydroxy-4-phenyl-piperidin-1-yl)-1-propanone compound having formula II or the enantiomer thereof using a catalyst system comprising ruthenium, a nonracemic chiral diphosphine ligand, a bidentate amine ligand selected from aminothioethers and achiral diamines, and a base.

BRIEF DESCRIPTION OF THE DRAWINGS

Not applicable

DETAILED DESCRIPTION OF THE INVENTION

Unless otherwise stated, the following terms used in the specification and claims have the meanings given below:

"Alkyl" means a linear saturated monovalent hydrocarbon radical or a branched saturated monovalent hydrocarbon radical or a cyclic saturated monovalent hydrocarbon radical, having the number of carbon atoms indicated in the prefix. For example, $(C_1-C_6)$alkyl is meant to include methyl, ethyl, n-propyl, 2-propyl, tert-butyl, pentyl, cyclopentyl, cyclohexyl and the like. For each of the definitions herein (e.g. alkyl, alkenyl, alkoxy, aralkyloxy), when a prefix is not included to indicate the number of main chain carbon atoms in an alkyl portion, the radical or portion thereof will have twelve or fewer main chain carbon atoms. A divalent alkyl radical refers to a linear saturated divalent hydrocarbon radical or a branched saturated divalent hydrocarbon radical having the number of carbon atoms indicated in the prefix. For example, a divalent $(C_1-C_6)$alkyl is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2-C_6)$ alkenyl is meant to include, ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, $(C_2-C_6)$alkynyl is meant to include ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Aryl" means a monocyclic or bicyclic aromatic hydrocarbon radical of 6 to 10 ring atoms which is substituted independently with one to four substituents, preferably one, two, or three substituents selected from alkyl, alkenyl, alkynyl, halo, nitro, cyano, hydroxy, alkoxy, amino, monoalkylamino, di-alkylamino and heteroalkyl. More specifically the term aryl includes, but is not limited to, phenyl, biphenyl, 1-naphthyl, and 2-naphthyl, and the derivatives thereof.

"Aralkyl" refers to a radical wherein an aryl group is attached to an alkyl group, the combination being attached to the remainder of the molecule through the alkyl portion. Examples of aralkyl groups are benzyl, phenylethyl, and the like.

"Heteroalkyl" means an alkyl radical as defined herein with one, two or three substituents independently selected from cyano, alkoxy, amino, mono- or di-alkylamino, thioalkoxy, and the like, with the understanding that the point of attachment of the heteroalkyl radical to the remainder of the molecule is through a carbon atom of the heteroalkyl radical.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, halo, nitro, cyano, hydroxy, alkoxy, amino, acylamino, monoalkylamino, di-alkylamino, heteroalkyl, More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

In a general sense, the present invention provides a method for the preparation of a chiral alcohol of formula IV (shown without stereochemistry) from a ketone of formula III. Suitable ketones for use in the present invention are those wherein $R^1$ and $R^2$ are different, and optionally, one or both of $R^1$ and $R^2$ have a chiral center.

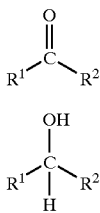

III

IV $R^1$ and $R^2$ in formulas III and IV are each independently a hydrocarbyl group. Suitable hydrocarbyl groups $R^1$ and $R^2$ include acyclic, cyclic, and heterocyclic hydrocarbyl groups, include saturated and unsaturated hydrocarbyl groups, include alkyl, heteroalkyl, aryl, heteroaryl, aralkyl, alkenyl, and alkynyl groups, as well as combinations thereof, and can be optionally substituted with one or more substituents that do not interfere with the reaction chemistry of the invention. $R^1$ and $R^2$ may be linked together in a cyclic structure. In a preferred combination of $R^1$ and $R^2$, $R^1$ is an optionally substituted alkyl group and $R^2$ is an optionally substituted aryl or heteroaryl group.

$R^1$ and $R^2$ may independently be chiral or achiral. As used herein, however, the adjective "chiral" in the term chiral alcohol specifically refers to the chirality at the carbon atom bearing each of $R^1$ and $R^2$, which chirality is produced by the hydrogenation of the keto group at that center. It does not refer to chirality that may be present in either $R^1$ or $R^2$.

In one particular embodiment, the ketone being reduced is selected from nonracemic 1-(4-hydroxy-phenyl)-2-(4-hydroxy-4-phenyl-piperidin-1-yl)-1-propanone having structural formula II or the enantiomer thereof, wherein R=H, and corresponding nonracemic ketones wherein R is a hydroxyl-protecting group. The nonracemic chiral alcohol produced therefrom is a corresponding 1-(4-hydroxy-phenyl)-2-(4-hydroxy-4-phenyl-piperidin-1-yl)-1-propanol compound of the formula I or a stereoisomer thereof, wherein R is hydrogen, or a corresponding chiral alcohol wherein R is a hydroxyl-protecting group. Preferred stereoisomers are the syn-enantiomers, (1S,2S)- and (1R,2R). Suitable hydroxyl protecting groups for R in formulas I and II can be found in, for example, Greene and Wuts, PROTECTIVE GROUPS IN ORGANIC SYNTHESIS, John Wiley & Sons, Chaps. 2 and 3, (1991). Preferably, the protecting groups are selected from trialkylsilyl protecting groups, allyl, benzyl, substituted benzyl, sulfonyl protecting groups, acyl groups, and alkoxymethyl protecting groups. A particularly preferred protecting group R is benzyl.

The racemic ketone corresponding to formula II with R=benzyl has been reported (U.S. Pat. No. 5,716,961). The enantiomeric ketones having formula II with R=benzyl, and its enantiomer can be prepared from the racemic ketone by diastereomeric salt resolution using enantiomeric di-O-benzoyl tartaric acid.

The ruthenium, nonracemic chiral diphosphine ligand, and bidentate amine ligand components of the catalyst system can be provided to the reaction mixture individually to form the reactive catalyst complex in situ or they can be provided as preformed complexes. Preformed complexes of ruthenium with the diphosphine ligand, or the bidentate amine ligand, or both can be used.

Examples of preformed complexes of the ruthenium with the diphosphine ligand include complexes represented by the formula $RuX_2LY_n$, wherein X represents a halogen atom or pseudo-halide group, preferably chloride or bromide, L represents the diphosphine ligand, Y represents a weakly coordinating neutral ligand, and n is an integer from 1 to 5. Examples of Y include trialkylamines, for examples triethylamine and tetramethylethylenediamine, and tertiary amides, for example dimethylformamide. Such complexes can be prepared by the reaction of the diphosphine ligand with a complex of the formula $[RuX_2(arene)]_2$, wherein examples of the arene include benzene, p-cymene, 1,3,5-trimethylbenzene, and hexamethylbenzene, in a solvent comprising Y.

Examples of preformed complexes of the ruthenium with both the diphosphine ligand and bidentate amine ligand include complexes represented by the formula $RuX_2LA$, wherein A is represents the bidentate amine ligand. Such complexes can be prepared by the reaction of the bidentate diamine ligand with a complex of the formula $RuX_2LY_n$ as described above.

The ruthenium component of the catalyst system, whether provided to the reaction mixture separately from the other components or used to form a preformed complex with the diphosphine ligand, the amine ligand, or both, can be provided by any ruthenium salt or complex capable of forming the active catalyst system in combination with the diphosphine ligand, the amine ligand, and the base. This can be determined by routine functional testing for ketone hydrogenation activity and enantioselectivity in the manner shown in the Examples. A preferred source of the ruthenium component is a complex of the formula $[RuX_2(arene)]_2$ as defined above.

Suitable nonracemic chiral diphosphine ligands for the present invention are bis-tertiary phosphines of the general formula $R^3R^4PR^aPR^5R^6$, wherein $R^3$, $R^4$, $R^5$, and $R^6$ are hydrocarbyl radicals, which may be the same or different, and $R^a$ is a hydrocarbyl diradical, any of which may be optionally linked in one or more cyclic structures. Suitable hydrocarbyl groups $R^3$, $R^4$, $R^5$, $R^6$, and diradicals thereof for $R^a$, include acyclic, cyclic, and heterocyclic hydrocarbyl groups, include saturated and unsaturated hydrocarbyl groups, include alkyl, heteroalkyl, aryl, heteroaryl, aralkyl, alkenyl, and alkynyl groups, and can be optionally substituted with one or more substituents that do not interfere with the reaction chemistry of the invention.

The chirality of the diphosphine ligand may reside in one or more of the hydrocarbyl groups $R^3$, $R^4$, $R^5$, $R^6$, in the bridging hydrocarbyl radical $R^a$, at phosphorus when two hydrocarbyl monoradicals on phosphorus are different ($R^3 \neq R^4$, or $R^5 \neq R^6$, or both), or combinations thereof. Chirality in the bridging hydrocarbyl diradical $R^a$ may be due to the presence of one or more chiral carbon centers or due to atropoisomerism.

Illustrative examples of nonracemic chiral diphosphines are the enantiomers of 2,2'-bis(diphenyl-phosphino)-1,1'-binaphthyl (BINAP), BINAP derivatives having one or more alkyl groups or aryl groups connected to one or both naphthyl rings, BINAP derivatives having 1–5 alkyl substituents on the phenyl rings bonded to phosphorus, for example 2,2'-bis-(di-p-tolylphosphino)-1,1'-binaphthyl (TolBINAP), 5,6,7,8,5',6',7',8'-octahydro-BINAP ($H_g$BINAP), 2,2'-bis(dicyclohexylphosphino)-6,6'-dimethyl-1,1'-biphenyl (BICHEP), 2,2'-bis(diphenylphosphino)-6,6'-dimethoxy-1,1'-biphenyl (MeOBIPHEP), 1-[1,2-bis-(diphenylphosphino)ferrocenyl] ethyldimethylamine (BPPFA), 2,3-bis(diphenylphosphino) butane (CHIRAPHOS), 1-cyclohexyl-1,2-bis (diphenylphosphino)ethane (CYCPHOS), 1-substituted 3,4-bis(diphenyl-phosphino)pyrolidine (DEGPHOS), 2,3-O-isopropylidene-2,3-dihydroxy-1,4-bis(diphenylphosphino)butane (DIOP), 1,2-bis[(O-methoxy-phenyl)phenylphosphino]ethane (DIPAMP), 2,5-disubstituted 1,2-bis(phospholano)benzenes (DuPHOS), for example 1,2-bis(2,5-dimethylphospholano)benzene (Me-DuPHOS), substituted 1,2-bis(phospholano)ethylenes (BPE), for example 1,2-bis(2,5-dimethylphospholano)ethylene (Me-BPE), 5,6-bis(diphenylphosphino)-2-norbornene (NORPHOS), N,N'-bis-(diphenylphosphino)-N,N'-bis(1-phenylethyl)ethylenediamine (PNNP), 1,2-bis-(diphenylphosphino)propane (PROPHOS), 2,4-bis(diphenylphosphino)pentane (SKEWPHOS), [6,7,8,9-tetrahydro-dibenzo[b,d]-[1,6]-dioxecin-1,14-diyl]-bis(diphenylphosphine) (C4-TunaPhos), 3,4-O-isopropylidene-3,4-dihydroxy-2,5-bis(diphenylphosphino)hexane (DIOP*), 1,2-bis{4,5-dihydro-3H-dinaphtho-[2,1-c:1',2'-e]phosphino}benzene (BINAPHANE), 1,1'-bis-{4,5-dihydro-3H-dinaphtho[2,1-c:1',2'-e]phosphino}ferrocene (f-BINAPHANE), 1,2-bis-[3,4-O-isopropylidene-3,4-dihydroxy-2,5-dimethylphospholanyl]-benzene (Me-KetalPhos), 1,1'-bis[3,4-O-isopropylidene-3,4-dihydroxy-2,5-dimethyl-phospholanyl]ferrocene (Me-f-KetalPhos), 2,2'-bis(diphenylphosphino)-1,1'-dicyclopentane (BICP), 1,2-bis-{2,5-disubstituted-7-phosphabicyclo[2.2.1]hept-7-yl}-benzenes (PennPhos), for example 1,2-bis-{2,5-dimethyl-7-phosphabicyclo[2.2.1]hept-7-yl}-benzene (Me-PennPhos), and 1,2-bis{1-phosphatricyclo[3.3.0.0]undecan-1-yl}benzene (C5-Tricyclophos), and equivalents thereto that are recognized by those skilled in the art.

Preferred nonracemic diphosphine ligands comprise a 2,2'-bis-(diorgano-phosphino)-1,1'-bis(cyclic) structure, wherein each cycle of the bis(cyclic) structure comprises three to eight carbon atoms, and wherein the 1,1', 2, and 2' carbon atoms in the bis(cyclic) structure are saturated. These ligands are described in detail in U.S. Pat. No. 6,037,500, incorporated herein by reference. The preferred nonracemic diphosphine ligands comprising a 2,2'-bis-(diorgano-phosphino)-1,1'-bis(cyclic) structure are of the formulas V and VI and their enantiomers, in which m is 1 to 6 and wherein each cycle of the bis(cyclic) structure may be unsubstituted as shown in formulas V and VI or further substituted with one or more substituents chosen from hydrocarbyl substituents and heteroatom containing substituents that do not interfere with the ketone hydrogenation chemistry, and wherein R' is a substituted or unsubstituted hydrocarbyl group selected from alkyl groups and aryl groups.

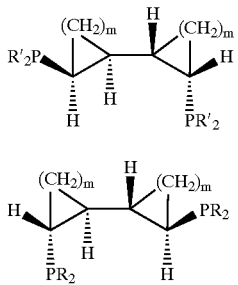

V

VI

Particularly preferred nonracemic diphosphine ligands are of the formula VII and its enantiomer, wherein Ar is an aryl group.

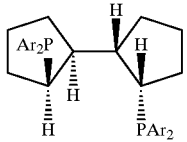

VII

Preferred aryl groups in formula VII are phenyl and mono-, di-, and trialkyl-phenyl, particularly wherein alkyl is methyl. Most preferred is phenyl, the ligand being a 2,2'-bis(diphenylphosphino)-1,1'-bicyclopentyl (BICP).

Suitable achiral diamine ligands for the present invention are bis-primary amines of the general formula $H_2NR^bNH_2$, wherein $R^b$ is an achiral hydrocarbyl diradical. Preferably, the hydrocarbyl diradical comprises at least three carbon atoms, more preferably at least four carbon atoms, and most preferably at least six carbon atoms, Suitable achiral hydrocarbyl diradicals for $R^b$ include acyclic, cyclic, and heterocyclic hydrocarbyl diradicals, include saturated and unsaturated hydrocarbyl diradicals, include alkyl, heteroalkyl, aryl, heteroaryl, aralkyl, alkenyl, and alkynyl diradicals, and can be optionally substituted with one or more substituents that do not interfere with the reaction chemistry of the invention.

The diamine may be achiral comprising no chiral carbon centers or it may be achiral comprising a meso compound. That is, the achiral hydrocarbyl diradical may contain one or more pairs of chiral carbon centers that are related in at least one of its conformations by a plane of symmetry. For example, while (S,S)- and (R,R)-1,2-diphenylethylenediamine are chiral enantiomers, (S,R)-1,2-diphenyl-ethylenediamine is an achiral meso compound. Preferably, the diamine is achiral comprising no chiral carbon centers.

Illustrative examples of achiral diamine compounds comprising at least three carbon atoms include 1,3-propylenediamine, 2-methyl-1,2-propylene-diamine, meso-2,3-butanediamine, meso-1,2-cyclopentanediamine, meso-1,2-cyclo-hexane-diamine, meso-1,2-cyclo-heptane-diamine, meso-1,2-diphenyl-ethylenediamines, meso-2,3-dimethyl-butane-1,2-diamine, 1,2-phenylenediamine, 2-aminobenzyl-amine, 1,8-diaminonaphthalene, and equivalents thereto that are recognized by those skilled in the art, any of which may be substituted with one or more substituents that do not interfere with the reaction chemistry of the invention, and provided such substitution preserves the achirality of the diamine.

Preferred achiral diamines are 1,2-phenylenediamine compounds and 1,8-diamino-naphthalene compounds, which may be substituted or unsubstituted. Suitable substituents include alkyl (e.g. 4,5-dimethyl-1,2-phenylenediamine), benzo (e.g. 9,10-diaminophenanthrene), and alkoxy (e.g, 1,3-benzodioxole-5,6-diamine).

Suitable amino-thioether ligands for the present invention are of the general formula $H_2NR^cSR^7$, wherein $R^7$ is a hydrocarbyl radical and $R^c$ is a hydrocarbyl diradical and which may be optionally linked in a cyclic structure. Suitable hydrocarbyl groups $R^7$ and diradicals thereof for $R^c$ include acyclic, cyclic, and heterocyclic hydrocarbyl groups, include saturated and unsaturated hydrocarbyl groups, include alkyl, heteroalkyl, aryl, heteroaryl, aralkyl, alkenyl, and alkynyl groups, and can be optionally substituted with one or more substituents that do not interfere with the reaction chemistry of the invention The amino-thioether ligand may be achiral, racemic chiral, or nonracemic chiral, preferably achiral.

Preferred amino-thioether ligands are selected from 2-(alkylthio)ethylamines, 2-(alkylthio)anilines, and equivalents thereto that are recognized by those skilled in the art. Most preferred are 2-(alkylthio)anilines. Preferably the alkyl group therein is selected from $C_1$ to $C_4$ alkyl groups. Most preferred are methyl and ethyl. Illustrative examples include 2-(methylthio)aniline and 2-(ethylthio)aniline.

Suitable bases include basic inorganic and organic salts, preferably selected from basic salts comprising a cation selected from an alkali metal cation, an alkaline earth cation, and quaternary ammonium cation and a basic anion selected from hydroxide and alkoxide anions. Examples include lithium, sodium, potassium, and quaternary ammonium salts of hydroxide, methoxide, ethoxide, isopropoxide, and t-butoxide.

In a further inventive embodiment of the invention, the base is selected from alkylguanidines, aminophosphazenes, and proazaphosphatranes.

Suitable alkylguanidines have the general formula VIII, wherein $R^8$, $R^9$, $R^{10}$, $R^{11}$, and $R^{12}$ are independently selected from hydrogen and alkyl groups, with the proviso that at least one of $R^8$, $R^9$, $R^{10}$, $R^{11}$, and $R^{12}$ is an alkyl group.

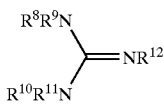

VIII

Preferably the alkylguanidine comprises two alkyl groups, more preferably three alkyl groups, even more preferably four alkyl groups, and most preferably five alkyl groups. Any of the alkyl groups $R^8$, $R^9$, $R^{10}$, $R^{11}$, and $R^{12}$ may be optionally linked in one or more cyclic structures. An illustrative example of a suitable tetraalkylguanidine base is 1,5,7-triazabicyclo[4.4.0]dec-5-ene and tetramethylguanidine. Illustrative examples of suitable pentalkylguanidines are 7-methyl-1,5,7-triazabicyclo[4.4.0]dec-5-ene and tetramethyl-2-t-butylguanidine.

Suitable aminophosphazenes have the general formula IX, wherein $R^{13}$ is selected from hydrogen and alkyl groups, $R^{14}$ is an alkyl group and the two $R^{14}$ groups on each —$NR^{14}$ group may optionally be linked in a cyclic structure, and x is an integer from zero to three.

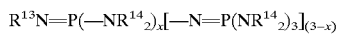   IX

Illustrative examples of suitable aminophosphazenes include N,N,N',N',N'',N''-hexa-methyl-phosphorimidic triamide ($R^{13}$=H, $R^{14}$=methyl, x=3, y=0), N'''-t-butyl-N,N,N', N',N'',N''-hexamethyl-phosphorimidic triamide ($R^{13}$=t-butyl, $R^{14}$=methyl, x=3, y=0), (t-butyl-imino)-tris(pyrrolidino)-phos-phorane ($R^{13}$=t-butyl, —$NR^{14}{}_2$=pyrrolidino, x=3, y=0), N'''-[N-ethyl-P,P-bis-(dimethylamino)phosphinimyl]-N,N,N',N',N'',N''-hexamethylphosphorimidic triamide ($R^{13}$=ethyl, $R^{14}$ methyl, x=2, y=1), and t-butyl-tris[tris(dimethyl-amino)-phosphoranylidene] phosphorimidic triamide ($R^{13}$=t-butyl, $R^{14}$=methyl, x=0, y=3).

Suitable proazaphosphatranes are described in U.S. Pat. No. 5,051,533 and have the general formula X, wherein $R^{15}$, $R^{16}$, and $R^{17}$ are independently selected from hydrogen and alkyl groups.

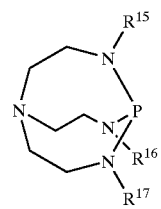

X

Preferably $R^{15}$, $R^{16}$, and $R^{17}$ are selected from $C_1$ to $C_1$ alkyl groups, most preferably methyl. An illustrative preferred proazaphosphatrane is 2,8,9-trimethyl-2,5,8,9-tetraaza-1-phosphabicyclo[3.3.3]undecane ($R^{15}$=$R^{16}$=$R^{17}$= Methyl).

The components of the catalyst system are each present in catalytic amounts, meaning less than stoichiometric relative to the ketone reactants. The minimum amount of the catalyst system relative to the ketone reactant may depend on the activity of the specific catalyst system composition, the specific ketone to be reacted, the hydrogen pressure, the gas-liquid mixing characteristics of the reaction vessel, the reaction temperature, the concentrations of the reactants and catalyst system components in the solution, and the maximum time allowed for completion of the reaction, and can be readily determined by routine experimentation. In typical embodiments, the mole ratio of the ruthenium component of the catalyst system to the ketone reactant is in the range from about 1/100 to about 1/100,000, preferably in the range from about 1/500 to about 1/10,000.

The mole ratio of the nonracemic diphosphine ligand to the ruthenium in the catalyst system is typically in the range from about 0.5 to about 2.0, preferably from about 0.8 to about 1.2, and most preferably is about 1. The mole ratio of the bidentate amine ligand to the ruthenium in the catalyst system is typically in the range from about 1 to about 50, and preferably from about 5 to about 20. The mole ratio of the base to the ruthenium in the catalyst system is typically in the range from about 1 to about 100, and preferably from about 1 to about 50.

The hydrogenation reaction may be conducted without solvent when the ketone itself is a liquid at the reaction temperature and capable of dissolving the catalyst system. More typically, the hydrogenation reaction is conducted in a solvent system that is capable of dissolving the catalyst system and is reaction-inert. The term solvent system is used to indicate that a single solvent or a mixture of two or more solvents can be used. The term reaction-inert it used to mean that the solvent system does not react unfavorably with the reactants, products, or the catalyst system. It does not mean that the solvent does not participate productively in the desired reaction. For example, while not wishing to be bound by theory, it is believed that when the base is selected from alkylguanidines, aminophosphazenes, or proazaphosphatranes and the solvent is selected from alcohol solvents, the alcohol solvent levels the base. That is, these bases deprotonate the alcohol to form an alkoxide base in the reaction solution.

The solvent system need not bring about complete solution of the ketone reactant or the chiral alcohol product. The ketone reactant may be incompletely dissolved at the beginning of the reaction or the chiral alcohol product may be incompletely dissolved at the end of the reaction, or both.

Representative solvents are aromatic hydrocarbons such as benzene, toluene, xylene; aliphatic hydrocarbons such as pentane, hexane, heptane; halogen-containing hydrocarbon solvents such as dichloromethane and chlorobenzene; alkyl ethers, polyethers, and cyclic ethers such as methyl-t-butyl-ether, dibutylether, diethoxymethane, 1,2-dimethnoxyethane, and tetrahydrofuran; ester solvents such as ethyl acetate, organic solvents containing heteroatoms such as acetonitrile, DMF and DMSO; and alcohol solvents such as methanol, ethanol, 2-propanol, t-butanol, benzyl alcohol and the like; and mixtures thereof. Preferably, the solvent system comprises an alcohol solvent. Most preferably, the alcohol solvent is 2-propanol.

In typical embodiments, the reaction is suitably conducted at a temperature from about −30° C. to about 100° C., more typically from about 0° C. to about 50° C., and most typically from about 20° C. to about 40° C. The hydrogen pressure in the reaction is typically at least about 1 atm., and typically in the range from about 1 atm. to about 100 atm. More typically, the hydrogen pressure is in the range from about 5 atm to about 20 atm.

The reaction rate and time to completion are dependent on the identities of the ketone reactant and the catalyst components, their absolute concentrations and relative ratios, the temperature, the hydrogen pressure, the gas-liquid mixing provided, and the other reaction conditions. Typically, the reaction is allowed to continue for sufficient time to complete the conversion of the ketone reactant. For typical ketone reactants, using the preferred catalyst systems described and the preferred reaction conditions described herein, the reaction is typically completed in a period of time in the range from about a few minutes to about 24 hours, more typically in the range from about 1 hour to about 10 hours.

The nonracemic chiral alcohol is typically formed in at least about 60% stereomeric excess, preferably at least about 70%, more preferably at least about 80%, and most preferably at least about 90%. These stereomeric excesses refer to the chirality at the hydroxyl-bearing carbon of the alcohol group generated by the hydrogenation of the ketone group. When the ketone is achiral, the chiral alcohol can be one of two enantiomers, and the enantiomer excess (e.e.) is the measure of stereomeric excess. When the ketone reactant is already chiral, the chiral alcohol product is a diastereomer, and diastereomeric excess (d.e.) is the formally appropriate measure of stereomeric excess. For example, when (2S)-1-(4-benzyl-oxy-phenyl)-2-(4-hydroxy-4-phenyl-piperidin-1-yl)-1-propanone is hydrogenated to (1S,2S)-1-(4-benz-oxy-phenyl)2-(4-hydroxy-4-phenyl-piperidin-1-yl)-1-propanol, the d.e. is the percent excess of the (1S,2S)-product vs. the nondiastereoselective product, defined as [(1S,2S)−(1R,2S)]/[(1S,2S)+(1R,2S)], and the measure of the stereoselectivity of the generation of the new chiral center at the 1-carbon. Accordingly, the term "nonracemic diastereomer" when used to refer to a nonracemic chiral alcohol product, refers to a product with an excess of one diastereomer vs. its diastereomer with the opposite chirality at the hydroxyl-bearing carbon. Typically, the nonracemic diastereomer is produced in at least 60% d.e., preferably 70% d.e., more preferably 80% d.e. and most preferably 90% d.e.

EXAMPLES

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Preparation 1

Preparation of [RuCl$_2$(S,S,S,S-BICP)(DMF)n]:

To 2.5 mg (10 microgram-atom Ru) [RuCl$_2$(benzene)]$_2$ and 5.5 mg (11 micromole) (S,S,S,S-2,2'-bis-(diphenylphosphino)-1,1'-bicyclopentyl (S,S,S,S-BICP) in a 100 ml Schlenk flask under nitrogen was added 10 ml anhydrous, deaerated dimethyl-formamide (DMF). The resulting orange solution was heated at 130° C. for 20 minutes, then evaporated to dryness at 60–90° C. under vacuum (10 mmHg). The resulting orange-red solid residue, comprising [RuCl$_2$(S,S,S,S-BICP)(DMF)n], was further dried at 60–90° C. under vacuum for at least an additional hour.

A stock solution of 125 micromolar [RuCl$_2$((S,S,S,S-BICP)(DMF)n] in isopropanol was prepared by dissolving the solid residue in 80 ml anhydrous, deaerated isopropanol and stored under nitrogen. Stock solutions of other concentrations and of [RuCl$_2$((R,R,R,R-BICP)(DMF)n] were similarly prepared.

Preparation 2

Preparation of (2S)-1-(4-benzyloxy-phenyl)-2-(4-hydroxy-4-phenyl-piperidin-1-yl)-1-propanone (Formula II, R-benzyl):

120 g (0.289 mol) racemic 1-(4-benzyloxy-phenyl)-2-(4-hydroxy-4-phenyl-piperidin-1-yl)-1-propanone and 1360 ml acetone were charged to a 3 liter flask equipped with a mechanical stirrer, a thermometer and a reflux condenser. The resulting solution was warmed to 50° C., then 105 g (0.293 mol) di-O-benzoyl-D-tartaric acid was added followed by a 200 ml acetone rinse. The solution was stirred at 50° C. and a suspended solid formed after about 25 minutes. The suspension was stirred as an additional 5 hours at 50° C., and then the mixture was cooled to room temperature over 1 hour. The suspension was filtered and the solid cake was washed with 500 ml acetone. The solid was dried at about 45° C. under vacuum (10 mmHg) overnight, giving 191 g (86% yield) (2S)-1-(4-benzyloxy-phenyl)-2-(4-hydroxy-4-phenyl-piperidin-1-yl)-1-propanone di-O-benzoyl-D-tartaric acid salt.

To a solution of 51.2 g (0.61 mol) sodium bicarbonate in 585 ml water was added 118 g (0.152 mol) (2S)-1-(4-benzyloxy-phenyl)-2-(4-hydroxy-4-phenyl-piperidin-1-yl)-1-propanone di-O-benzoyl-D-tartaric acid salt followed by 350 ml ethyl acetate. The resulting mixture was stirred at 20–25° C. for 2 hours. The ethyl acetate layer was separated, washed with saturated aqueous sodium bicarbonate(2×50 ml), dried over MgSO$_4$/Na$_2$SO$_4$ (40 g/40 g) for one hour, filtered, and combined with ethyl acetate rinses (2×80 ml) of the filtered drying salts. The ethyl acetate solution was reduced in volume to about 100 ml at about 75° C. and cooled to room temperature. 1000 ml heptane was slowly added with stirring, and the resulting suspension was stirred for an additional 30 minutes. The suspension was filtered and the solid was washed with heptane (2×100 ml). The solid was dried at 80° C. under vacuum (10 mmHg) for three hours, giving 58 g (92% yield from the salt) (2S)-1-(4-benzyl-oxy-phenyl)-2-(4-hydroxy-4-phenyl-piperidin-1-yl)-1-propanone as the free base, 98.6% e.e.

Recrystallization of the (2S)-ketone Free Base:

45 g of this free base was dissolved in 250 ml refluxing methanol, 50 ml 5 mM aqueous sodium hydroxide was added with rapid stirring, and the resulting solution was cooled to ambient temperature with a water bath, forming a suspension. After one hour, the suspended solid was filtered, washed with 5 mM aqueous sodium hydroxide (100 ml), then with 4:1 methanol:5 mM aqueous sodium hydroxide (2×100 ml). The solid was dried at 80° C. overnight under vacuum (10 mmHg), giving 43 g (95.6% recovery) (2S)-1-(4-benzyl-oxy-phenyl)-2-(4-hydroxy-4-phenyl-piperidin-1-yl)-1-propanone, 98.8% e.e. This material was used for hydrogenation reactions.

(2R)-1-(4-benzyloxy-phenyl)-2-(4-hydroxy-4-phenyl-piperidin-1-yl)-1-propanone may be similarly prepared using di-benzoyl-L-tartaric acid.

Example 1

This Example illustrates the process of the invention wherein the ruthenium catalyst system comprises a nonracemic diphosphine ligand comprising a 2,2'-bis(diorganophosphino)-1,1'-bis(cyclic) structure, an achiral diamine ligand and an alkoxide base.

In a dry nitrogen-filled glovebox, a glass autoclave liner was charged with 20 ml 125 micromolar (2.5 micromoles) [RuCl$_2$((S,S,S,S-BICP)(DMF)n] in isopropanol, 90 ml isopropanol, 0.5 ml 0.1 M (50 micromoles) 4,5-dimethyl-1,2-diamino-benzene in isopropanol. After stirring for about 2 minutes, 5.2 g (12.5 millimole) (2S)-1-(4-benzyl-oxy-phenyl)-2-(4-hydroxy-4-phenyl-piperidin-1-yl)-1-propanone was added, followed by 0.5 ml 0.2 M (100 micromoles) sodium isopropoxide in isopropanol. The glass liner containing the resulting suspension was sealed in an autoclave, which was then removed from the glovebox. The gas phase in the autoclave was replaced by hydrogen at 18 bar. The gas-liquid mixture was then stirred for 22 hours. Chiral HPLC analysis of the reaction mixture showed 98.8% conversion of the ketone to give (1S,2S)-1-(4-benzoxyphenyl)-2-(4-hydroxy-4-phenyl-piperidin-1-yl)-1-propanol with 99.1% d.e.

The product was isolated by filtering the resulting suspension, washing the solid with isopropanol (3×20 ml), and drying it under vacuum to obtain the product as a white solid in >80% yield, >98% purity, and >99% d.e.

Example 2

This Example illustrates the process of the invention wherein the ruthenium catalyst system comprises a nonracemic diphosphine ligand comprising a 2,2'-bis(diorganophosphino)-1,1'-bis(cyclic) structure, an achiral diamine ligand and an alkylguanidine base.

In a dry nitrogen-filled glovebox, a glass vial was charged with 1.0 ml 250 micromolar (0.25 micromoles) [RuCl$_2$((S,S,S,S-BICP)(DMF)n] in isopropanol, 9 ml isopropanol, 50 microliters 0.1 M (5.0 micromoles) 4,5-dimethyl-1,2-diamino-benzene in isopropanol. After stirring for about 2 minutes, 520 mg (1.25 millimole) (2S)-1-(4-benzyl-oxy-phenyl)-2-(4-hydroxyphenyl-piperidin-1-yl)-1-propanone was added, followed by 75 microliters 0.1 M (7.5 micromoles) tetramethyl-2-t-butylguanidine in isopropanol. The glass liner containing the resulting suspension was sealed in an autoclave, which was then removed from the glovebox. The gas phase in the autoclave was replaced by hydrogen at 18 bar. The gas-liquid mixture was then stirred for 20 hours. Chiral HPLC analysis of the reaction mixture showed 99.5% conversion of the ketone to give (1S,2S)-1-(4-benzoxyphenyl)-2-(4-hydroxy-4-phenyl-piperidin-1-yl)-1-propanol with 99.6% d.e.

Example 3

This Example illustrates the process of the invention wherein the ruthenium catalyst system comprises a nonracemic diphosphine ligand comprising a 2,2'-bis(diorganophosphino-1,1'-bis(cyclic) structure, an amino-thioether ligand and an alkylguanidine base.

The procedure was the identical to Example 2 with the exemptions that 50 microliters 0.1 M (5.0 micromoles) 2-(methylthio)aniline in isopropanol was used instead of the 4,5-dimethyl-1,2-diamino-benzene solution. Chiral HPLC analysis of the reaction mixture showed 99.0% conversion of the ketone to give (1S,2S)-1-(4-benzoxyphenyl)-2-(4-hydroxy-4-phenyl-piperidin-1-yl)-1-propanol with 99.3% d.e.

Example 4

This Example illustrates the process of the invention wherein the ruthenium catalyst system comprises a nonracemic diphosphine ligand comprising a 2,2'-bis(diorganophosphino)-1,1'-bis(cyclic) structure, an amino-thioether ligand and an alkoxide base.

The procedure was the identical to Example 3 with the exceptions that 25 microliters 0.2 M (5.0 micromoles) sodium isopropoxide in isopropanol was used instead of the tetramethyl-2-t-butylguanidine solution. Chiral HPLC analysis of the reaction mixture showed 99.1% conversion of the ketone to give (1S,2S)-1-(4-benzoxyphenyl)-2-(4-hydroxy-4-phenyl-piperidin-1-yl)-1-propanol with 99.4% d.e.

Example 5

(2R)-1-(4-benzyl-oxy-phenyl)-2-(4-hydroxy-4-phenyl-piperidin-1-yl)-1-propanone was hydrogenated in isopropanol solution at room temperature under 18 bar hydrogen for one hour at using [RuCl$_2$((R,R,R,R-BICP)(DMF)n], 4,5-dimethyl-1,2-diamino-benzene and sodium isopropoxide in the mole ratios ketone:Ru:BICP:diamine:base= 500:1:1:5:20. Chiral HPLC analysis of the reaction mixture showed 98.8% conversion of the ketone to give (1R,2R)-1-(4-benzoxyphenyl)-2-(4-hydroxy-4-phenyl-piperidin-1-yl)-1-propanol with 98.2% d.e.

Example 6

The procedure was identical to Example 5 with the exception that the (2S) enantiomer of the 1-(4-benzyl-oxy-phenyl)-2-(4-hydroxy-4-phenyl-piperidin-1-yl)-1-propanone was reacted, again using the (R,R,R,R)-BICP ligand. Chiral HPLC analysis of the reaction mixture showed 99.5% conversion of the ketone to give (1R,2S)-1-(4-benzoxy-phenyl)-2-(4-hydroxy-4-phenyl-piperidin-1-yl)-1-propanol with 92.0% de.

This example shows the production of an anti enantiomer of the product.

Examples 5 and 6 taken together show that the chirality generated at the 1-carbon by reduction of the ketone to the alcohol is predominantly controlled by the chirality of the catalyst comprising the chiral diphosphine ligand, and only relatively weakly influenced by the chirality at the 2-carbon of the ketone. Whether the (2R)-ketone (Example 5) or the (2S)-ketone (Example 6) is reduced using the (R,R,R,R,)-BICP ligand, the chirality generated in the alcohol is predominantly (1R) by greater than 90% d.e.

Examples 7–27

(2S)-1-(4-benzyl-oxy-phenyl)-2-(4-hydroxy-4-phenyl-piperidin-1-yl)-1-propanone was hydrogenated in isopropanol solution at room temperature for 4 to 14 hours under 18 bar hydrogen using a catalyst system provided by [RuCl$_2$((S,S,S,S-BICP)(DMF)n], a bidentate amine ligand, and a base in the mole ratios ketone:Ru:BICP:amine:base= 500:1:1:5:20. The amine ligand, the base, the conversion of the ketone, and the d.e. of the resulting (1S,2S)-1-(benzoxy-phenyl)-2-(4-hydroxy-4-phenyl-piperidin-1-yl)-1-propanol are given in Table 1. Abbreviations are as follows:

| | |
|---|---|
| Me2PhDN: | 4,5-dimethylaminophenylene-1,2-diamine |
| MeSAN: | 2-(methylthio)aniline |
| EtSAN: | 2-(ethylthio)aniline |
| iPrSAN: | 2-(isopropylthio)aniline |
| EtSEN: | 2-(ethylthio)ethylamine |
| iPrONa: | sodium isopropoxide |
| H-P1: | N,N,N',N',N'',N''-hexamethyl-phosphorimidic triamide |
| tBu-P1: | N'''-t-butyl-N,N,N',N',N'',N''-hexamethyl-phosphorimidic triamide |
| Et-P2: | N'''-[N-ethyl-P,P-bis(dimethyl-amino)phosphinimyl]-N,N,N',N',N'',N''-hexa-methyl-phosphorimidic triamide |
| tBu-P4: | t-butyl-tris[tris(dimethyl-amino)-phosphoranylidene]-phosphor-imidic triamide |
| TAPBU: | 2,8,9-trimethyl-2,5,8,9-tetraaza-1-phospha-bicyclo[3.3.3]-undecane |
| TBD: | 1,5,7-triazabicyclo[4.4.0]dec-5-ene |
| MeTBD: | 7-methyl-1,5,7-triazabicyclo[4.4.0]dec-5-ene |
| MetG: | tetramethylguanidine |
| tBuMe4G: | tetramethyl-2-t-butylguanidine |
| BTPP: | (t-butyl-imino)-tris(pyrrolidino)-phosphorane |

TABLE I

| Example | amine | base | conv. (%) | d.e. (%) |
|---|---|---|---|---|
| 7 | Me2PhDN | iPrONa | 98.6 | 98.1 |
| 8 | Me2PhDN | H-P1 | 99.6 | 96.6 |
| 9 | Me2PhDN | tBu-P1 | 99.5 | 97.9 |
| 10 | Me2PhDN | Et-P2 | 99.5 | 98.0 |
| 11 | Me2PhDN | tBu-P4 | 99.6 | 98.6 |
| 12 | Me2PhDN | TBD | 99.6 | 98.6 |
| 13 | Me2PhDN | TAPBU | 98.6 | 98.1 |
| 14 | Me2PhDN | MeTBD | 99.5 | 98.2 |
| 15 | Me2PhDN | Me4G | 60.7 | 98.0 |
| 16 | Me2PhDN | tBuMe4G | 99.5 | 98.4 |
| 17 | MeSAN | iPrONa | 99.4 | 94.9 |
| 18 | MeSAN | tBuMe4G | 98.7 | 94.4 |
| 19 | MeSAN | MeTBD | 99.3 | 94.3 |
| 20 | MeSAN | BTPP | 99.4 | 94.9 |
| 21 | MeSAN | tBu-P1 | 99.5 | 94.8 |
| 22 | EtSAN | iPrONa | 99.1 | 98.4 |
| 23 | EtSAN | tBuMe4G | 99.4 | 98.3 |
| 24 | EtSAN | MeTBD | 99.5 | 98.4 |
| 25 | EtSAN | BTPP | 99.4 | 98.5 |
| 26 | iPrSAN | BTPP | 66.5 | 94.2 |
| 27 | EtEN | iPrONa | 99.2 | 63.3 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for the preparation of a nonracemic diastereomer selected from the group consisting of (1R,2R)-, (1R,2S)-, (1S,2R)- and (1S,2S)-1-(4-hydroxy-phenyl)-2-(4-hydroxy-4-phenyl-piperidin-1-yl)-1-propanol compounds of the structural formula I,

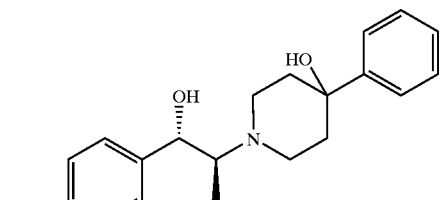

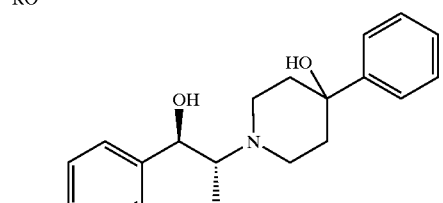

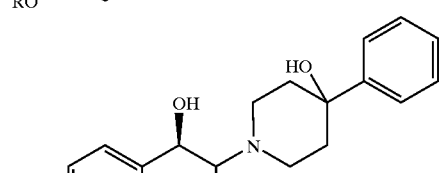

and

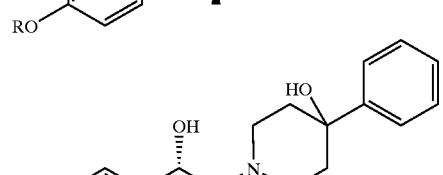

wherein R is selected from hydrogen and hydroxyl protecting groups, comprising hydrogenating a corresponding nonracemic ketone selected from 1-4-hydroxy-phenyl)-2-(4-hydroxy-4-phenyl-piperidin-1-yl)-1-propanone compounds of the structural formula II,

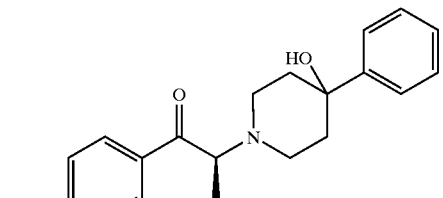

and

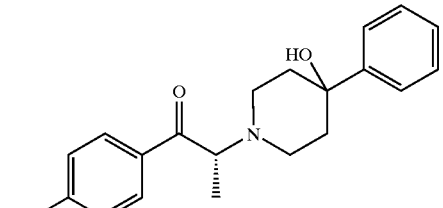

in the presence of a catalyst system comprising ruthenium, a nonracemic diphosphine ligand, a bidentate amine ligand selected from amino-thioethers and achiral diamines, and a base to produce said nonracemic diastereomer in a diastereomeric excess of at least 70%.

2. The process of claim 1 wherein the nonracemic diphosphine ligand comprises a 2,2'-bis(diorganophosphino)-1,1'-bis(cyclic) structure.

3. The process of claim 2 wherein the nonracemic diphosphine ligand is selected from enantiomers of diphosphine ligands having the structural formula

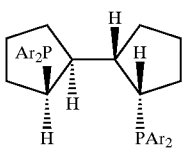

wherein Ar is an aryl group.

4. The process of claim 3 wherein Ar is phenyl.

5. The process of claim 1 wherein the bidentate amine ligand is an amino-thioether.

6. The process of claim 5 wherein the amino-thioether is a 2-(alkylthio)aniline.

7. The process of claim 6 wherein the 2-(alkylthio)aniline is selected from 2-(methylthio)aniline and 2-(ethylthio)aniline.

8. The process of claim 1 wherein the bidentate amine ligand is an achiral diamine.

9. The process of claim 8 wherein the achiral diamine comprises no chiral carbon centers.

10. The process of claim 8 wherein the achiral diamine is a 1,2-phenylene-diamine.

11. The process of claim 1 wherein the base is selected from basic inorganic and organic salts, alkylguanidines, aminophosphazenes, and proazaphosphatranes.

12. The process of claim 11 wherein the base is selected from alkylguanidines, aminophosphazenes, and proazaphosphatranes.

13. The process of claim 12 wherein the base is an alkylguanidine.

14. The process of claim 13 wherein the base is a pentaalkylguanidine.

15. The process of claim 1 wherein the hydroxyl protecting group is benzyl.

16. The process of claim 15 wherein the diastereomer is a syn-diastereomer.

17. The process of claim 16 wherein the syn-diastereomer is the (1S,2S) diastereomer.

18. The process of claim 16 wherein the syn-diastereomer is formed in at least about 90% diastereomeric excess.

19. A process for the preparation of (1S,2S)-1-(4-benzoxy-phenyl)-2-(4-hydroxy-4-phenyl-piperidin-1-yl)-1- by catalytic hydrogenation of (2S)-1-(4-benzyl-phenyl)-2-(4-hydroxy-4-phenyl-piperidin-1-yl)-1-propanone using a catalyst system comprising ruthenium, a (S,S,S,S)-2,2'-bis-(diarylphosphino)-1,1'-dicyclopentane ligand, a 1,2-phenylene diamine ligand, and a base.

20. A process for the preparation of (1S,2S)-1-(4-benzoxy-phenyl)-2-(4-hydroxy-4-phenyl-piperidin-1-yl)-1- by catalytic hydrogenation of (2S)-1-(4-benzyl-phenyl)-2-(4-hydroxy-4-phenyl-piperidin-1-yl)-1-propanone using a catalyst system comprising ruthenium, a (S,S,S,S)-2,2'-bis-(diarylphosphino)-1,1'-dicyclopentane ligand, a 2-(alkylthio)aniline ligand, and a base.

* * * * *